United States Patent [19]

Caron et al.

[11] Patent Number: 5,409,477

[45] Date of Patent: Apr. 25, 1995

[54] SOLUTION ADMINISTRATION APPARATUS WITH ORIFICE FLOW CONTROL DEVICE

[75] Inventors: Lois L. Caron, McHenry; Nicholaos A. Drivas, Des Plaines; Con A. Lasaitis, Waukegan; William L. Rudzena, McHenry, all of Ill.

[73] Assignee: Abbott Laboratories, Abbott Park, Ill.

[21] Appl. No.: 125,979

[22] Filed: Sep. 23, 1993

[51] Int. Cl.$^6$ .................................. A61B 19/00
[52] U.S. Cl. ............................ 604/407; 604/403; 604/405; 604/408; 604/905; 604/246; 604/251; 128/912; 128/DIG. 12
[58] Field of Search ....... 128/912, DIG. 12, DIG. 26; 604/403, 246, 407, 251, 118, 122, 408, 409, 905, 405, 406, 280, 283

[56] References Cited

U.S. PATENT DOCUMENTS

| | | | |
|---|---|---|---|
| 3,533,400 | 10/1970 | Palich | 604/118 |
| 3,620,500 | 11/1971 | Santomieri | 604/246 |
| 4,588,396 | 5/1986 | Stroebel et al. | 604/246 |
| 4,927,418 | 5/1990 | Dake et al. | 604/264 |
| 5,100,390 | 3/1992 | Lubeck et al. | 604/158 |
| 5,248,300 | 9/1993 | Bryant et al. | 128/DIG. 12 |
| 5,290,238 | 3/1994 | Crass et al. | 604/246 |

*Primary Examiner*—Randall L. Green
*Assistant Examiner*—P. Zuttarelli
*Attorney, Agent, or Firm*—T. M. Breininger; H. T. Thibault

[57] ABSTRACT

A solution administration apparatus for patient care, for use with an associated solution administration system, which apparatus includes a laser drilled orifice flow control device to provide a controlled, predetermined flow rate of solution to the patient. The apparatus includes a tubing set and a laser drilled orifice flow restrictor, formed in a body, and in fluid communication therewith, for use with an associated fluid supply container. The system provides a controlled, predetermined flow rate of solution to the patient which is independent of, and relatively constant over minor variations in solution supply pressure and viscosity.

9 Claims, 3 Drawing Sheets

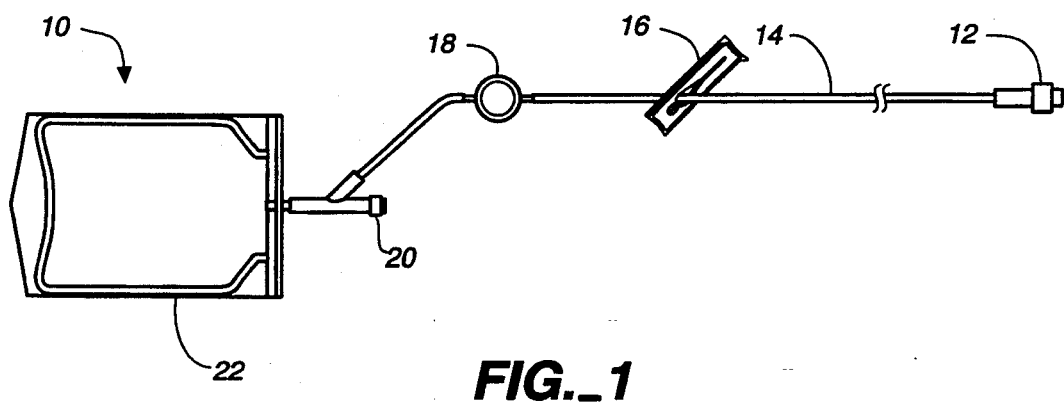
FIG._1
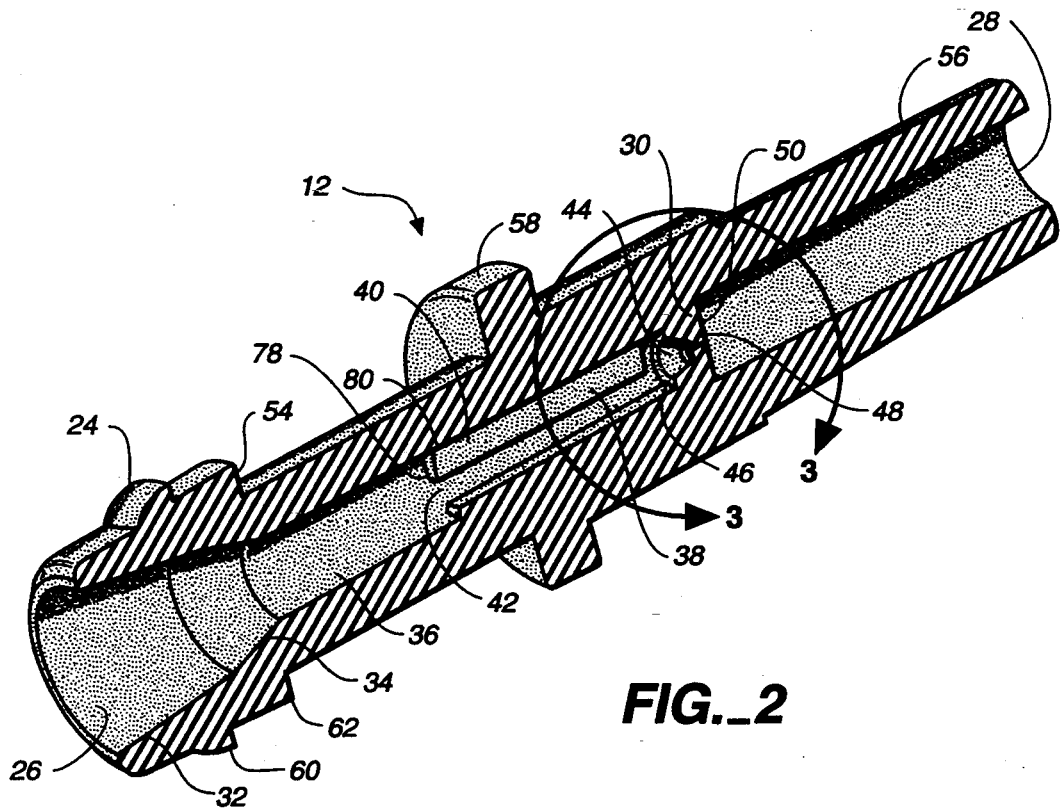
FIG._2

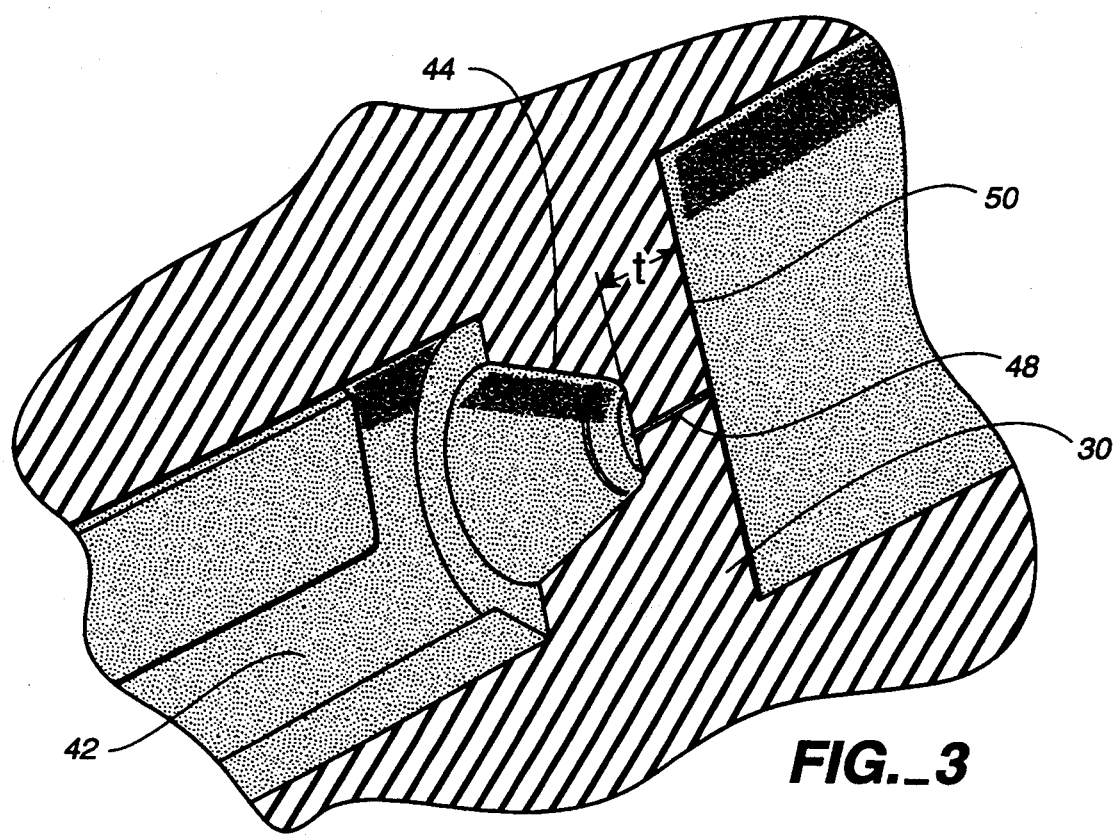
FIG._3
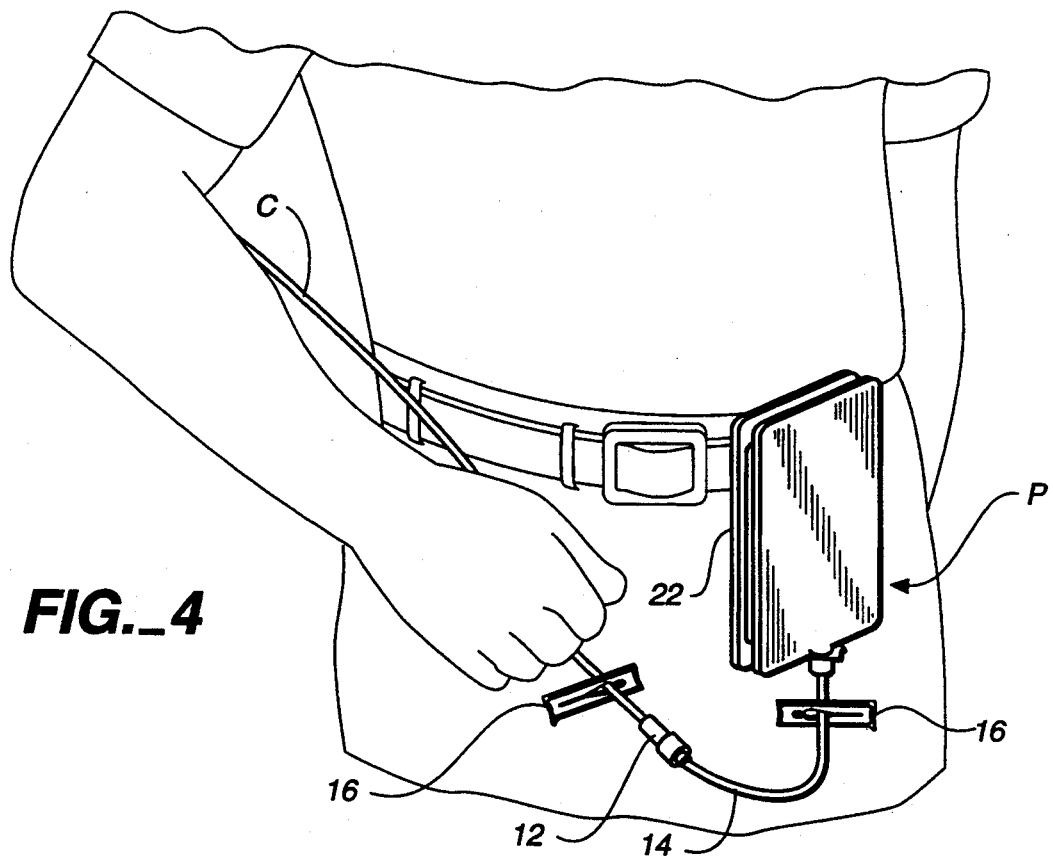
FIG._4

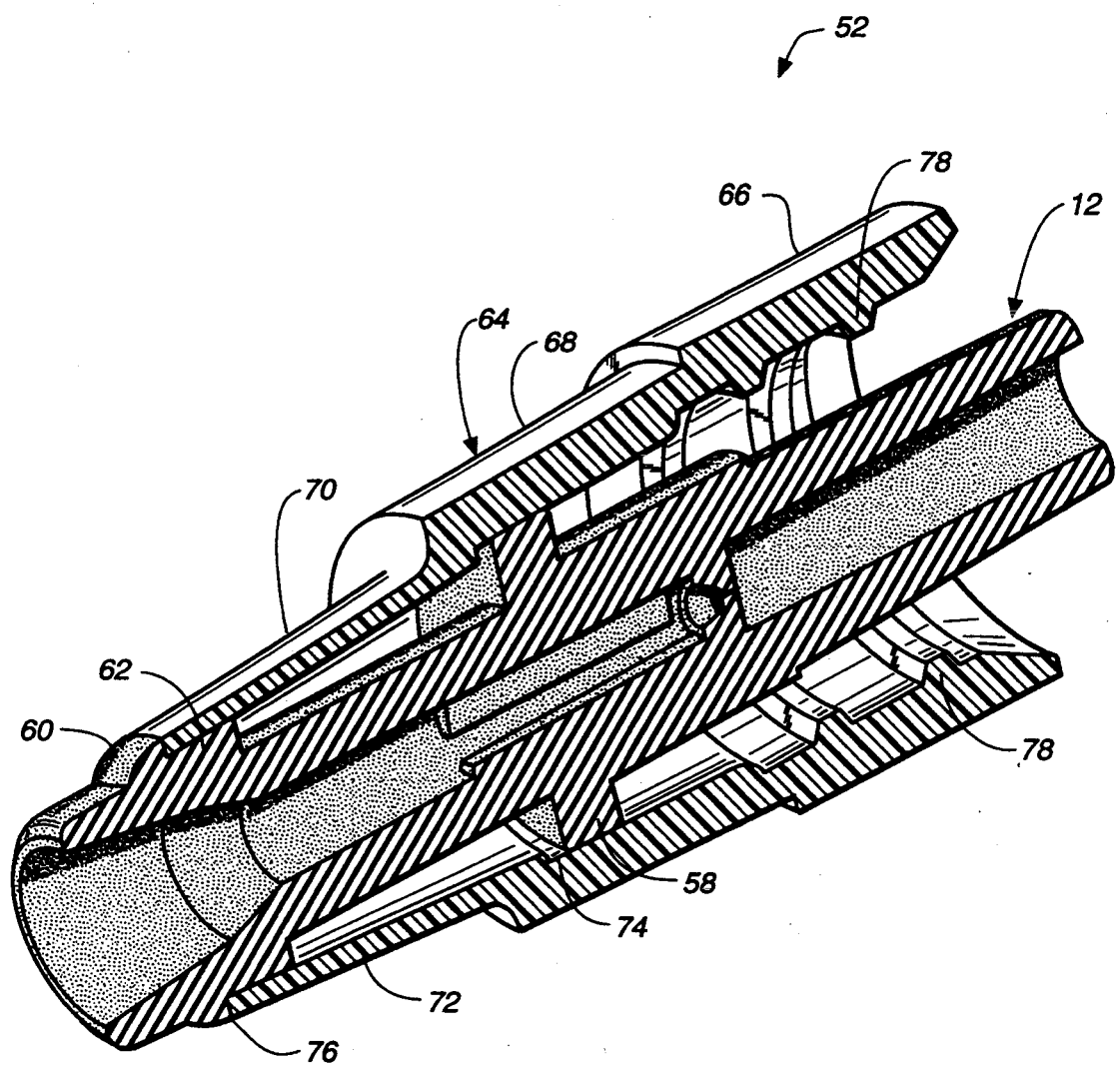
FIG._5

SOLUTION ADMINISTRATION APPARATUS WITH ORIFICE FLOW CONTROL DEVICE

FIELD OF THE INVENTION

This invention relates to infusion systems for the administration of solutions for patient care and more particularly to a solution administration apparatus including a laser drilled orifice flow restrictor for providing accurate and predetermined solution flow under varying pressure and fluid viscosity conditions.

BACKGROUND OF THE INVENTION

Inpatient and outpatient therapy often requires the administration of an intravenous solution to a patient through a device such as a catheter to permit infusion of medicament or other solution as required. The rate of flow of solution into the patient's body is an extremely important variable which can be affected by the pressure of the solution supply and the fluid viscosity.

It is present practice to use a capillary type flow restrictor which includes a relatively long, small diameter tube (on the order of 0.0015 inches) in order to regulate the flow of medicament or solution to the patient. However, capillary type flow restrictors are inherently problematic. First, because of the nature of the device, the upstream pressure, or the solution pressure, will have a great affect on the rate of flow of solution through the capillary. Second, the fluid viscosity also greatly affects the rate of flow through the capillary. As such, when the viscosity of the fluid increases, the rate of flow of solution or medicament decreases.

Because of the inherent nature of capillary type flow restrictors, in order to maintain a constant flow rate through the capillary, either the solution feed pressure has to be maintained at a constant level or the fluid viscosity, vis-a-vis fluid temperature, must be maintained at a constant level. As a result, to effectuate the proper solution feed to a patient, the patient is required to be relatively immobile to assure that the fluid conditions, i.e., solution feed pressure and viscosity, remain at the required levels.

The present invention contemplates a highly accurate solution feed system which comprises a solution feed container, a tubing set and an orifice flow restrictor. The orifice flow restrictor operates in a manner which is relatively independent of the solution feed pressure and viscosity, therefore making it much more advantageous for use in both inpatient and outpatient application for continual solution or medicament feed to a patient.

SUMMARY OF THE INVENTION

The present invention contemplates a solution administration system for infusion by a controlled, predetermined fluid flow, which system includes a solution supply container, a tubing set and a laser drilled orifice flow restrictor. The solution supply container may be the collapsible bag or self-contained pressurized type for mobile patient solution administration. The supply container has a fluid port to which is connected a tubing set including a length of tubing. An orifice flow restrictor is formed within a restrictor body and is part of the male fitting of a typical Luer fitting connector in fluid connection with the aforesaid tubing. The female fitting of the Luer connector is in fluid communication with a catheter for patient infusion of solution.

The orifice is comprised of a small diameter fluid passage drilled by laser through an orifice plate which has a predetermined cross-sectional flow area and which defines a flow control passage. The orifice plate creates a boundary between the inlet and outlet ports of the body. The orifice plate is relatively thin; however, the thickness is dependent upon the diameter of the orifice drilled therethrough. To maintain the fluid flow characteristics of an orifice, the maximum ratio of plate thickness to orifice diameter is 10:1. The actual orifice diameter will vary as required by the precise flow of solution for the particular patient's requirements.

In accordance with the present invention, the orifice flow restrictor delivers a predetermined and accurate flow of solution to a patient. Unlike capillary restrictors, the orifice restrictor is relatively unaffected by minor variations in supply solution pressure or viscosity. Moreover, because of the interrelationship between solution feed viscosity and temperature, the orifice restrictor is also relatively unaffected by minor variations in temperature as well.

As a result of the relatively determinable fluid flow characteristics, the solution administration apparatus of the present invention can be used with relative ease and confidence in a hospital or clinical situation, and can be used in the treatment of mobile patients. The present invention can be used to provide the required solution feed to a patient while freeing the patient from immobilization in a hospital bed or other clinically administered situations. Because the fluid flow characteristics are relatively constant over varying supply solution pressures, viscosities and temperatures, the present invention is particularly suited for home patient care.

Other features and advantages of the present invention will be apparent from the following detailed description, the accompanying drawings, and the appended claims.

BRIEF DESCRIPTION OF THE DRAWINGS

FIG. 1 is a schematic illustration of the solution administration system and orifice flow restrictor embodying the principles of the present invention;

FIG. 2 is a cross-sectional perspective view of the orifice flow restrictor of the present invention, as shown, formed within a body;

FIG. 3 is an enlarged partial cross-sectional perspective view of the orifice flow restrictor;

FIG. 4 illustrates an embodiment of the present solution administration system for mobile patient use; and FIG. 5 is a cross-sectional view of the orifice flow restrictor of FIG. 2 mounted in an associated collar portion, and constituting the male fitting of a typical Luer fitting connector.

DETAILED DESCRIPTION OF PREFERRED EMBODIMENTS

While the present invention is susceptible of embodiment in various forms, there is shown in the drawings and will be hereinafter be described a presently preferred embodiment, with the understanding that the present disclosure is to be considered as an exemplification of the invention, and is not intended to limit the invention to the specific embodiment illustrated.

Referring generally to FIG. 1, there is shown a typical arrangement 10 for administering solution to a patient including an orifice flow restrictor 12, a tubing set 14, an in-line clamp 16, an air elimination filter 18, a Y-connector 20, and an associated solution supply container 22, as shown by the exemplary intravenous solution supply bag. Air elimination filter 18 can be operably interpose anywhere in tubing set 14 between flow restrictor 12 and container 22.

Referring now to FIGS. 2 and 3, an orifice flow restrictor 12 of the present invention is shown more fully in detail. The flow restrictor 12 includes an elongated body 24, with an inlet port 26, and an outlet port 28 formed therein. Separating the inlet and outlet ports 26, 28 is a barrier-like wall or orifice plate 30. Inlet port 26 has first and second inward distal tapers 32, 34 to a substantially constant diameter medial section 36. The distal portion 38 of medial section 36 has a plurality of raised longitudinal ribs 40 (four in a current embodiment) along the interior wall 42 extending to orifice plate 30. Proximal surface 46 of plate 30 is formed with a tapered nipple shaped depression 44 therein, as best seen in FIG. 2.

An orifice 48 is drilled through plate 30, which defines a flow control passage, and which extends from about the center of depression 44 to outlet port 28. The orifice 48 has a predetermined cross-sectional flow area which provides accurate predetermined flow communication between inlet port 26 and outlet port 28. Orifice 48 is produced by drilling through plate 30 with a laser or other narrow frequency light emitting cutting device. The diameter of orifice 48 can range from about 0.0011 to about 0.0050 inches dependent upon the rate of administration of solution as required for the particular patient.

In the embodiment of the orifice flow restrictor 12 described and shown in the associated figures, the body 24 was formed from a polycarbonate material. The orifice 48 was drilled to a diameter of 0.0029 inches, through orifice plate 30, which has a thickness, t, of 0.012 inches with a tolerance of +0.002 inches. The orifice 48 was drilled using a Resonetics, Eximer laser. The ratio of the thickness of plate 30, between the base of depression 44 and the distal surface 50 of plate 30, to the diameter of orifice 48, is limited to a maximum of 10:1. Conversely, orifice 48 must be at least one tenth of the length, L, of the flow control passage through plate 30 at a point adjacent to the orifice 48. In the flow restrictor 12 as illustrated, the ratio of thickness, t, to the diameter of orifice 48 is about 5.2:1.

Outlet port 28 extends from the distal surface 50 of orifice plate 30 to the outlet 52. Outlet port 28 has a substantially constant circular cross-section along its length as best seen in FIG. 2.

Referring now to FIGS. 2 and 5, which best illustrate the exterior features of body 24, it is noted that the following description and attendant figures are exemplary of the male end of a typical Luer fitting connector 52 which is in the nature of a collar and insert arrangement, and which is common in the medical arts. Body 24 has a proximal portion 54 and a distal portion 56 separated therebetween by medial ring 58. Proximal portion 54 has first and second lips 60, 62 formed thereon. Collar fitting 64 of the connector 52 has distal, medial and proximal portions 66, 68, 70 of successively smaller diameter. Proximal portion 70 has a frusto-conically tapered wall 72 which forms a collar 76 at the end thereof. A lip 74 extends radially inward, internal to collar fitting 64 at about medial portion 68.

In assembly, body 24 is inserted into collar fitting 64 such that collar 76 abuts lip 60 and medial ring 58 is positioned adjacent to lip 74. This locked in arrangement prevents axial movement, while permitting independent rotational movement, of body 24 relative to collar fitting 64. Collar fitting 64 and body 24 can then be connected to an associated female adapter (not shown) of a Luer fitting for subsequent fluid communication to a patient through an associated catheter (not shown).

Solution feed is provided to orifice flow restrictor 12 through a length of tubing 14. The tubing inner diameter and length must provide less flow restriction than the orifice. Tubing 14 is permanently affixed to body 24, by inserting tubing 14 into inlet port 26 and urging into body 24. Over insertion of tubing 14 is prevented by tubing stops 78 located at the proximal ends 80 of ribs 40. The tubing is affixed to body 24 by application of a solvent or other permanent means. In a preferred construction, body 24 is fabricated from a medical quality material such as polycarbonate or the like, capable of sterilization by irradiation or other appropriate means.

FIG. 4 shows a typical arrangement for administering a solution to a patient utilizing a wearable intravenous solution delivery system including an administration system in accordance with the present invention. The wearable delivery system includes an arrangement P for pressurizing solution supply container 22, a tubing set 14, in-line clamps 16, an orifice flow restrictor 12 formed within a typical Luer fitting connector and a catheter C.

The wearable delivery system provides the advantages attendant with patient mobility during the administration of solution. Because the orifice flow restrictor 12' has a predetermined flow rate, there is no need or possibility for the patient to change the solution flow rate during use.

As noted above, the present system 10 is intended to provide constant predetermined flow rates by use of a laser drilled orifice flow restrictor 12. The flow rate, as determined by the size of the orifice 48, is constant and independent of slight variations in fluid supply pressure and viscosity, a problem which is inherent in the capillary type flow restrictors presently known in the art. Additionally, the simplicity of design results in a minimal number of parts requiring less labor and providing a greater level of confidence of controlling solution administration. These attendant advantages allow for a reduced cost, disposable system.

From the foregoing, it will be observed that numerous modifications and variations can be effected without departing from the true spirit and scope of the novel concept of the present invention. It is to be understood that no limitation with respect to the specific embodiments illustrated is intended or should be inferred. The disclosure is intended to cover by the appended claims all such modifications as fall within the scope of the claims.

What is claimed is:

1. A solution administration apparatus for use with an associated container having a flow port, comprising:
   a connector for connection in fluid communication with the flow port of said container;
   at least one length of tubing jointed in fluid communication with said connector; and
   a flow control device displaced from the connector, said flow control device comprising a body defining an inlet port and an outlet port joined in fluid communication with said tubing, and a fluid flow passage between said ports for accommodating flow of solution through said flow control device, a plate of a pre-determined thickness disposed within said fluid flow passage and an orifice enabling fluid flow and having a predetermined cross-sectional flow area passing through said plate, the relationship between the thickness of the plate and the diameter of the orifice enabling a controlled, predetermined flow of solution through said device and associated tubing connected to the outlet port to a catheter connected to the tubing for administration to a patient.

2. The solution administration apparatus in accordance with claim 1 wherein said orifice is laser drilled and is about 0.0011 to about 0.0050 inches in diameter.

3. The solution administration apparatus in accordance with claim 1 wherein said orifice is about 0.0029 inches in diameter.

4. The solution administration apparatus in accordance with claim 1 wherein the ratio of the thickness of said plate to the diameter of said orifice is no more than 10:1.

5. The solution administration apparatus in accordance with claim 1 further including an air eliminating filter located in said tubing set operably interposed between said container and said flow control device.

6. The solution administration apparatus in accordance with claim 1 further including a Luer locking collar having said flow control device formed therein.

7. The solution administration apparatus in accordance with claim 1 wherein the body of said flow control device is fabricated from polycarbonate.

8. A flow control device for use with a solution administration apparatus, said flow control device comprising:

a body defining an inlet port and an outlet port, and a fluid flow passage therebetween for accommodating flow of solution therethrough, a plate of a pre-determined thickness disposed within said fluid flow passage and an orifice enabling fluid flow and having a predetermined cross-sectional flow area formed by laser drilling passing through said plate, said orifice having a diameter of about 0.0011 to about 0.0050 inches, and wherein a ratio of the thickness of the plate to the diameter of the orifice is no more than 10:1, the relationship between the thickness of the plate and the diameter of the orifice enabling a controlled, predetermined flow of solution through said device for administration to a patient.

9. The flow control device of claim 8 further including a Luer locking collar having said flow control device formed therein.

* * * * *